United States Patent [19]
Abrams et al.

[11] Patent Number: 5,490,763
[45] Date of Patent: Feb. 13, 1996

[54] PUMP FOR SHEAR SENSITIVE FLUIDS

[76] Inventors: Andrew L. Abrams, 26 Imperial Ave., Westport, Conn. 06880; Christopher M. Gaylo, 22 Landing La., Princeton Junction, N.J. 08550

[21] Appl. No.: 306,877

[22] Filed: Sep. 15, 1994

[51] Int. Cl.[6] .................................................. F04D 29/18
[52] U.S. Cl. ........................ 415/206; 415/900; 416/185; 416/223 B
[58] Field of Search ................................. 415/206, 900; 416/179, 182, 185, 223 B

[56] References Cited

U.S. PATENT DOCUMENTS

| | | | |
|---|---|---|---|
| 1,896,089 | 2/1933 | Krogh | 416/185 |
| 3,261,297 | 7/1966 | Daniel | 416/182 |
| 3,734,640 | 5/1973 | Daniel | 416/185 |
| 4,072,612 | 2/1978 | Daniel | |
| 4,606,698 | 8/1986 | Clausen et al. | 415/900 |
| 4,898,518 | 2/1990 | Hubbard et al. | 415/900 |
| 5,137,424 | 8/1992 | Daniel | |
| 5,213,474 | 5/1993 | Daniel | |

Primary Examiner—F. Daniel Lopez
Assistant Examiner—James A. Larson
Attorney, Agent, or Firm—Hayes, Soloway, Hennessey, Grossman & Hage

[57] ABSTRACT

A centrifugal pump for shear sensitive fluids includes a pump housing defining an interior volume. An impeller comprising at least two vanes is rotatably mounted in the housing. The impeller vanes, which preferably are airfoil-shaped, are spaced from the interior housing of the pump whereby to leave a gap between the vanes and the pump housing so as to permit a portion of the fluid in the spacing to flow smoothly over the top contour of the impeller vanes.

8 Claims, 4 Drawing Sheets

PUMP FOR SHEAR SENSITIVE FLUIDS

FIELD OF THE INVENTION

The present invention relates to pumps, more particularly of the centrifugal type in which a series of spaced vanes moves in a circular path, and fluid enters at a point within the circular path and moves outward through the revolving vanes and leaves the pump at a point at the periphery of the circular path. The invention has particular utility in connection with the pumping of shear sensitive fluids such as non-Newtonian, thixotropic fluids as well as blood or other biological fluids, and will be described in connection with such utility, although other utilities are contemplated.

BACKGROUND OF THE INVENTION

Conventional centrifugal type pumps comprise an impeller bearing a plurality of vanes. The impeller is rotated about an axis in a chamber having a central inlet and a peripheral outlet for the pumped fluid. While conventional centrifugal type pumps are widely used in industry, the shear forces imparted to the fluid by conventional centrifugal type pumps presents a problem in the case of shear sensitive fluids such as non-Newtonian, thixotropic fluids as well as blood or other biological fluids. While shear forces imparted to the fluid can be reduced by reducing the rotational speed of the impeller's vanes, reducing the rotational speed of the vanes results in a substantial reduction in flow volume and pressure.

It is therefore an object of the present invention to provide a centrifugal type pump for shear sensitive fluids that overcomes the aforesaid and other disadvantages of the prior art. A more specific object of the present invention is to provide a centrifugal type pump characterized by improved volume flow rates with lower fluid shear rates than current centrifugal type pumps.

SUMMARY OF THE INVENTION

The present invention solves aforesaid and other disadvantages of the prior art by providing a centrifugal type pump comprising a pump housing defining an interior volume in which is contained an impeller comprising at least two vanes having airfoil-shaped contours. The airfoil-shaped vanes are spaced from the interior housing of the pump whereby to leave a gap or space between the vanes' apex and the pump housing. The combination of the airfoil-shaped contours of the vanes and a spacing between the vanes' apex and the housing produces a high pressure slip stream that attaches at one edge to the stationary upper housing at the other edge of the rotating impeller whereby to reduce turbulence and shear stress on fluid as it is drawn into and accelerated through the pump.

BRIEF DESCRIPTION OF THE DRAWINGS

Still other objects and advantages of the present invention will become apparent from the following detailed description, taken in conjunction with the accompanying drawings, in which like numerals depict like parts and wherein.

DETAILED DESCRIPTION OF THE INVENTION

Figure 1:
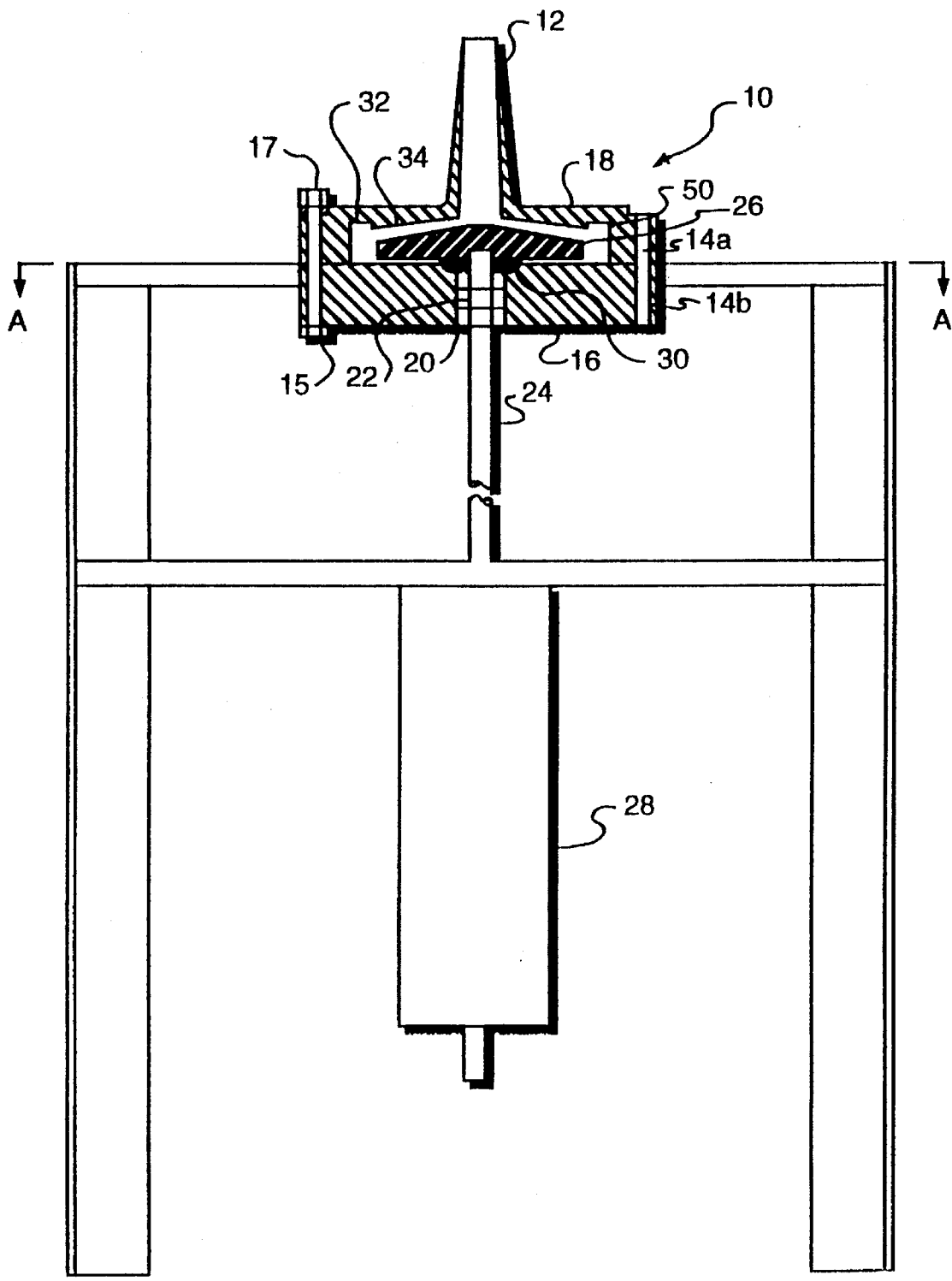
FIG. 1 is a partial sectional view of a preferred embodiment of the invention.
Figure 2:
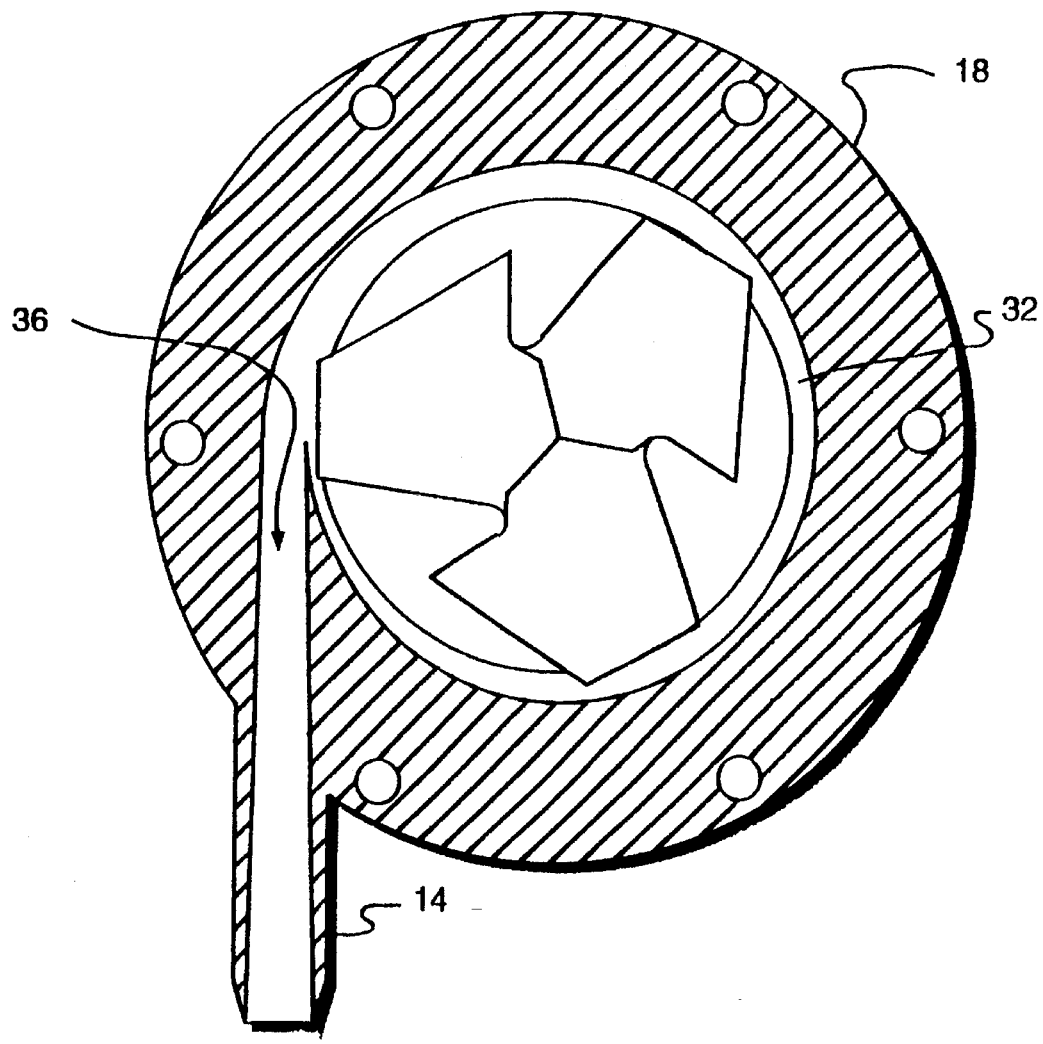
FIG. 2 is a top plan view, partly in section of the pump shown in FIG. 1 taken along line A—A.

Referring to the drawings, a pump made in accordance with the present invention comprises a generally cylindrical casing 10 having a central inlet 12 and a peripheral outlet 14. Casing 10 is comprised of two principal parts, a base 16 and a cover 18 which comprises inlet 12 and outlet 14.

Base 16 comprises a generally flat cylindrical disk having a central aperture 20 in which is press-mounted a bearing 22 which in turn accommodates an impeller drive shaft 24 which is rigidly secured at one end thereof to an impeller plate 26 and at its other end to a rotary drive means 28. Drive means 28 may comprise a conventional electric motor, but in preferred embodiment comprises a magnetic rotary drive. Drive means 28 is of conventional construction and will not be further described. A seal 30 is press-fitted in aperture 20 and surrounds shaft 24 to seal the casing against leakage.

Cover 18 is generally cup-shaped and, as noted supra, comprises an integrally formed central inlet 12 and a peripheral outlet 14. A radially outwardly expanding recess 32 is formed in the upper interior wall of casing 18 and communicates at location 36 with outlet 14.

Cover 18 and base 16 are shown held together by means of nuts 15 and bolts 17 which extend through holes 19a, 19b in cover 18 and base 16, respectively. However, a preferred embodiment may be glued or bonded together to form a permanent assembly.

Figure 3:
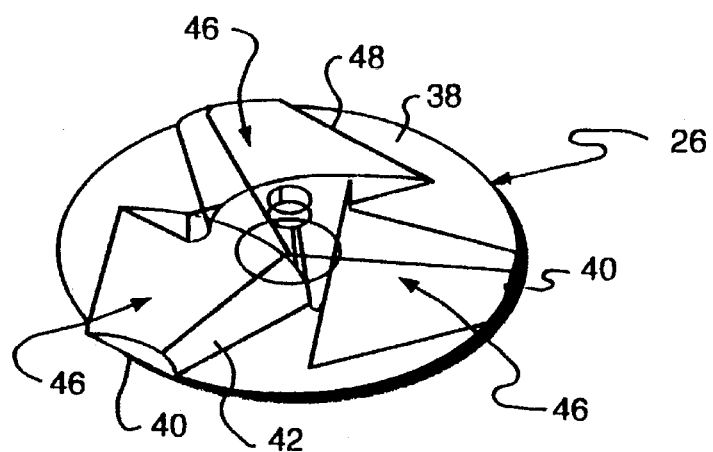
FIG. 3 is a perspective view showing the impeller suitable for use in the pump according to the invention.
Figure 4:
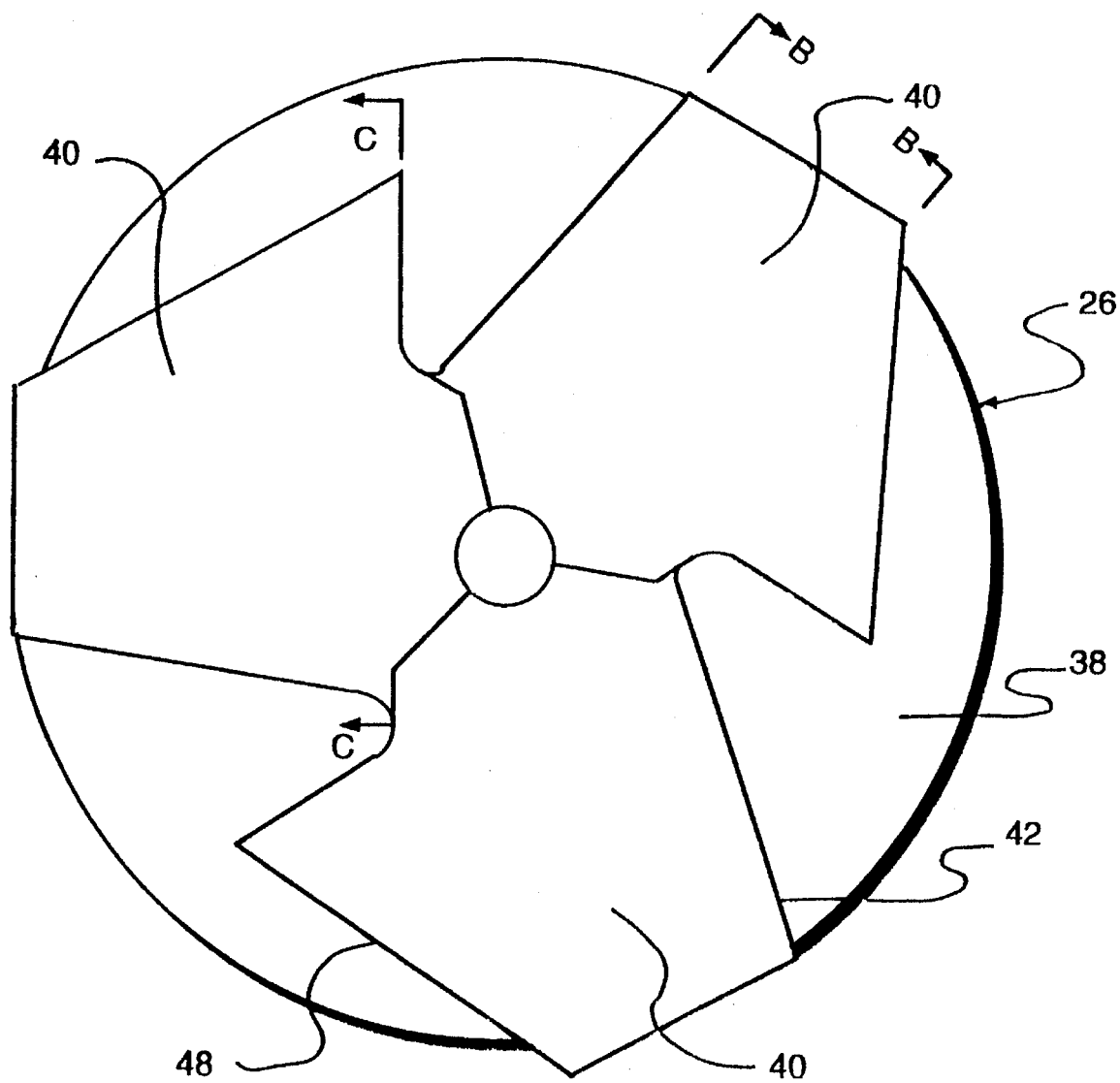
FIG. 4 is a top plan view of the impeller shown in FIG. 3.
Figure 5:
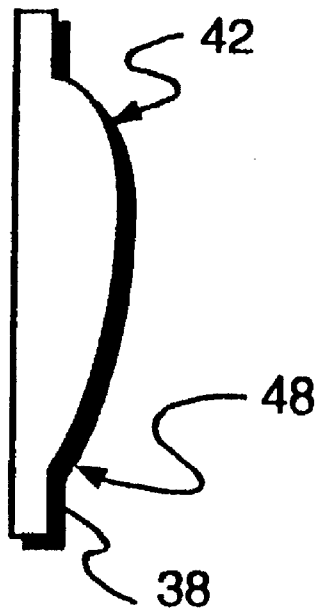
FIG. 5 is a sectional view taken along line B—B of FIG. 4.
Figure 6:
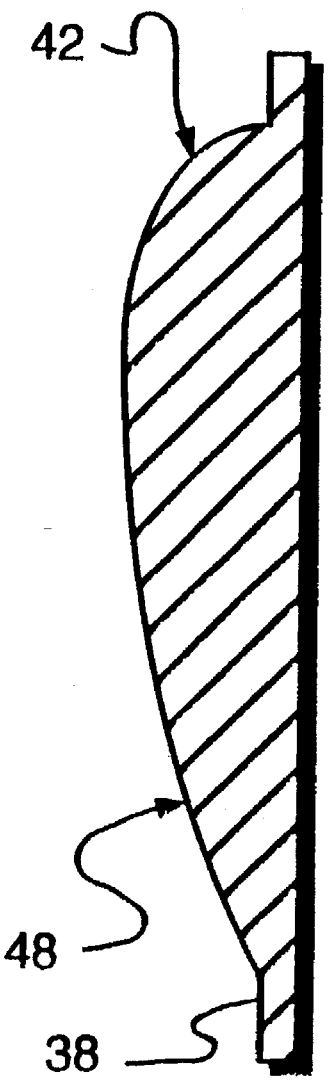
FIG. 6 is a section view taken along line C—C of FIG. 4.

A feature and advantage of the present invention is the use of an airfoil type impeller 26 which is undersize relative to the pump interior. Referring in particular to FIGS. 3–5, impeller 26 comprises a planar plate 38 comprising a plurality of equi-angularly spaced identical blades or vanes 40. Vanes 40, which are in the shape of an airfoil each comprise a smoothly contoured, rounded leading edge 42 which blends into a generally parabola-shaped top surface 46 running to trailing edge 48 which terminates at the top surface of plate 38. In order to reduce turbulence, vanes 40 preferably are shaped as truncated wedges in plan view. In a preferred embodiment, the shape may be that of a laminar-flow airfoil.

Referring again to FIG. 1, as can be seen, the impeller 26 has a size and shape such that there is a gap or space 50 between the apexes of the impeller and the interior surfaces of the pump housing. As a result, when the impeller rotates, a portion of the fluid in the casing flows smoothly over the top contour 46 of the impeller vanes. Thus, only a portion of the fluid in the pump is subjected to the high pressure region which forms forward of each airfoil's apex, with the result that local turbulence and shear are substantially reduced as compared to a conventional centrifugal pump.

Although the present invention has been described in connection with a preferred embodiment thereof, it will be appreciated that modifications thereof remain possible without departing whatsoever from the scope and spirit of the invention, which is defined by the appended claims.

What is claimed is:

1. A centrifugal pump for shear sensitive fluids comprising a pump housing having an interior surface defining an interior volume, and an impeller rotatably mounted within said pump housing around a central axis, and comprising at least two airfoil-shaped vanes, each of which has a smoothly contoured, rounded leading edge which blends into a generally parabola-shaped top surface, the leading edge of each vane having a cross-sectional shape which is narrowest adjacent the periphery of the impeller, and the vanes are spaced from the interior surface of the pump housing leaving a gap between the top surface of the vanes and the interior surface of the pump housing whereby a portion of the fluid in the housing flows smoothly over the top surface of the vanes whereby to minimize turbulence and shear.

2. A pump according to claim 1, wherein said vanes are shaped as truncated wedges, in plan view.

3. A pump according to claim 1, wherein said impeller comprises a circular plate from which said vanes depend.

4. A pump according to claim 3, wherein said impeller comprises three airfoil-shaped vanes.

5. A pump according to claim 4, wherein said vanes are equi-angularly spaced on said plate.

6. A pump according to claim 1, and further comprising means for rotatably driving the impeller.

7. A pump according to claim 6, wherein said drive means comprises an electric motor.

8. A pump according to claim 6, wherein said drive means comprises a magnetic rotary drive.

* * * * *